United States Patent [19]

Saito

[11] 4,449,931

[45] May 22, 1984

[54] TOOL FOR MAKING SEPARATED TOOTH MODEL

[75] Inventor: Koji Saito, Shiga, Japan

[73] Assignee: Kyoto Ceramic Co., Ltd., Japan

[21] Appl. No.: 356,828

[22] Filed: Mar. 10, 1982

[30] Foreign Application Priority Data

Mar. 17, 1981 [JP] Japan .............................. 56-37937[U]
Dec. 28, 1981 [JP] Japan .............................. 56-212275

[51] Int. Cl.³ .......................................... A61C 19/00
[52] U.S. Cl. .................................. 433/74; 433/34
[58] Field of Search ............ 433/74, 53, 60, 41, 433/45

[56] References Cited

U.S. PATENT DOCUMENTS

| | | | |
|---|---|---|---|
| 538,204 | 4/1895 | Traphagen | 433/41 |
| 2,619,725 | 12/1952 | Roeser | 433/60 |
| 3,226,827 | 1/1966 | Spalten | 433/74 |
| 3,360,860 | 1/1968 | Roland | 433/45 |
| 3,436,827 | 4/1969 | Dew | 433/34 |
| 3,702,027 | 11/1972 | Marshall et al. | 433/34 |
| 3,896,548 | 7/1975 | Zahn | 433/74 |
| 3,937,773 | 2/1976 | Huffman | 433/74 |
| 4,021,916 | 5/1977 | Spalten | 433/74 |
| 4,265,619 | 5/1981 | Lucki et al. | 433/74 |

FOREIGN PATENT DOCUMENTS

| | | | |
|---|---|---|---|
| 800874 | 1/1951 | Fed. Rep. of Germany | 433/34 |
| 2835094 | 2/1980 | Fed. Rep. of Germany | 433/60 |

*Primary Examiner*—John J. Wilson
*Attorney, Agent, or Firm*—Spensley, Horn, Jubas & Lubitz

[57] ABSTRACT

Tool for making separated tooth model comprising a tray having a plurality of holes each made vertically in the surface thereof, and plural pins each capable of being engaged with the holes so that head portions of the pins are positioned above the surface of the tray.

7 Claims, 14 Drawing Figures

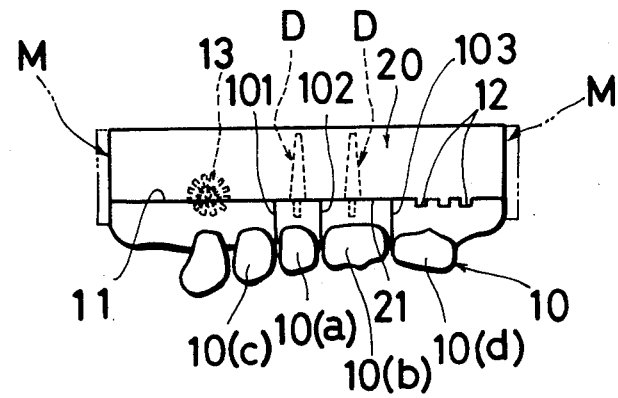
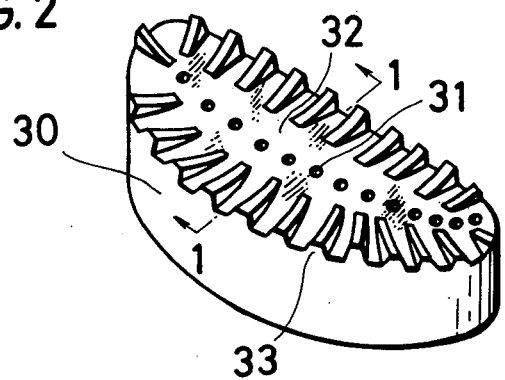
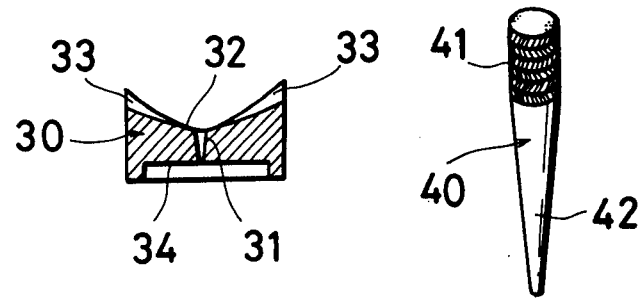

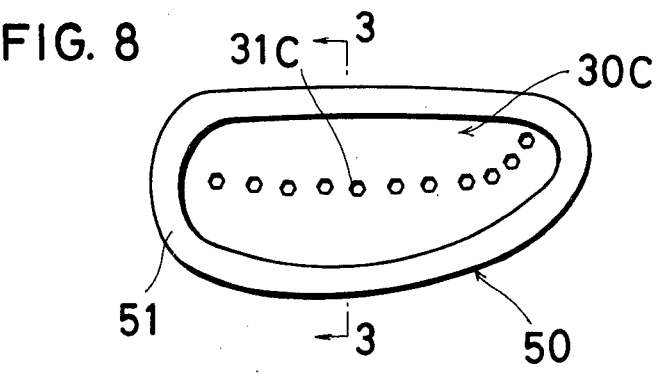
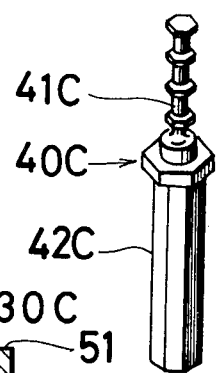
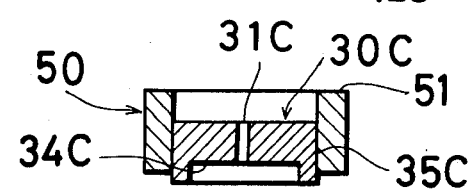
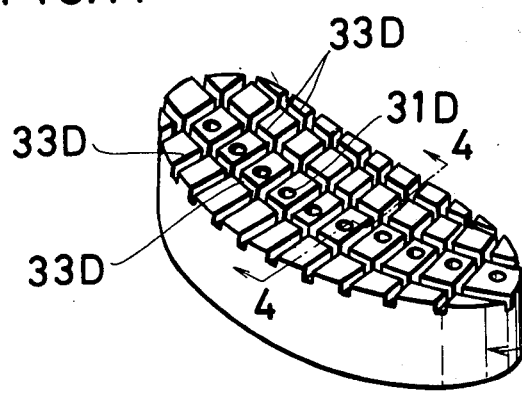
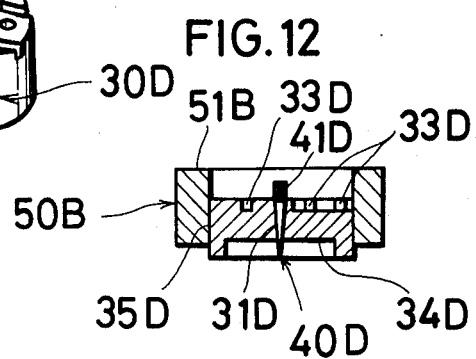

TOOL FOR MAKING SEPARATED TOOTH MODEL

This invention relates to a tool for making a separated tooth model or models from a plaster teeth row model.

Previously, separated tooth models were made from a teeth row model in a following manner.

As shown in FIG. 1 of accompanying drawings, back surface 11 of a plaster teeth row model 10 is flatly finished, and the teeth row model 10 is drilled in the back surface 11 at portions of tooth model 10(a), 10(b) which are desired to be separated. Then dowel pins D are engaged with the holes made by the foregoing drilling so that the dowel pins D are respectively positioned vertically, and the head portions of the pins are fastened by plaster. In the back surface 11 at portions of teeth row models 10(c), 10(d) which are to be left, roughness 12 is made, or metallic connecting pieces 13 are embedded. Subsequently, the back surface 11 at the portions of the tooth models 10(a), 10(b) which are desired to be separated is applied with plaster for separation, and the circumference of the teeth row model 10 is surrounded by a soft sheet material M mainly composed of wax or natural resin. The new plaster 20 is poured into the enclosure of the sheet material so that the leg portions of the dowel pins D are embedded in the plaster. After the poured plaster has been hardened, the teeth row model 10 is cut at both sides 101, 102, 103 of the tooth models 10(a), 10(b) which are desired to be separated so that gaps made by cutting reach surface 21 of the newly hardened plaster 20. Thus, the separated tooth models 10(a), 10(b) are obtained.

However, in the foregoing works, it takes at least thirty minutes to have the dowel pins fastened respectively by poured plaster after making holes in the back surface 11 of the teeth row model 10 at portions which are expected to be the back surface 11 of the tooth models 10(a), 10(b) desired to be separated, and engaging the dowel pins D with the holes. Further, it is difficult to engage the dowel pins D with the holes vertically, and where the dowel pins D have not been engaged vertically, it is difficult to take out the separated tooth models 10(a), 10(b). Accordingly, considerable time and skill are required to engage the dowel pins with the holes. In addition, after the teeth row model 10 is cut to separate, the separated tooth models have a tendency of rattling because of clearances which have been the made by cutting, and it is feared that this may seriously affect manufacturing of the crown of the tooth.

An object of the invention is to provide a tool for making separated tooth models, said tool enabling unskilled men to make precise separated tooth models from a plaster teeth row model in short time.

Another object of the invention is to provide a tool for making separated tooth models which do not rattle owing to clearances made by the cutting after the teeth row model has been cut.

Other objects of the invention appear in the accompanying drawings and the detailed explanation hereinafter described.

According to the before-mentioned objects, the invention discloses a tool for making separated tooth models comprising a tray having a plurality of holes made vertically in the surface of the tray and plural pins each capable of being engaged with said holes so that head portions of the pins are positioned above the surface, and another tool for making separated tooth models comprising a tray having a plurality of holes made vertically in the surface of the tray, plural pins each capable of being engaged with said holes so that the head portions of the pins are positioned above the surface, and a frame member releasably fastened around the side wall of the tray so as to form an embankment around the surface of the tray.

According to the invention, separated tooth models are obtained in a following manner.

Pins are vertically engaged with holes in the tray, the holes being located at positions corresponding to both the back surface of the tooth models to be separated and the back surface of the rest of a plaster teeth row model, the back surface of which has been flatly finished. Plaster is poured into the surface of the tray so that head portions of the pins are embedded in the plaster. The foregoing teeth row model is put on the plaster, and adheres to the plaster. After the plaster has been hardened, the teeth row model is cut at both sides of the tooth models desired to be separated and then the separated tooth models are obtained. For the purpose of decreasing the amount of the plaster which falls of the surface of the tray, it may be possible to form in the surface of the tray a sunken portion which is gradually deepened from the circumference of the surface to the central portion of the surface. Also, it may be possible to provide a frame member around the surface of the tray so as to form an embankment around the surface. Furthermore, for the purpose of preventing the tooth models from rattling after the tooth models have been separated, the invention has following three measures. Namely, to form a roughness in the surface of the tray, to arrange at least two rows of holes in the surface so that both a pin engaged with a hole belonging to one row and a pin engaged with a hole belonging to the other row may support a tooth model to be separated, and so that both another pin engaged with another hole belonging to one row and another pin engaged with another hole belonging to the other row may support the rest of the teeth row model, and to engage the pins with the holes so that the pins may not be revolved and taken out of the holes after the plaster has been hardened. Since the holes of the tray are made vertically, the pins engaged with the holes are vertically orientated. This makes it easy to take out the separated tooth models after cutting for separation.

Hereinafter an embodiment of the invention will be illustrated in detail making reference to the accompanying drawings, in which:

FIG. 1 is an explanatory diagram showing how to make separated tooth models in accordance with a prior method.

FIGS. 2 to 5 inclusive show an embodiment of the invention.

FIG. 2 is a perspective view of a tray.

FIG. 3 is a sectional view taken along the line 1—1 of FIG. 2

FIG. 4 is an enlarged perspective view of a pin.

FIG. 6 is a perspective view of a tray.

FIG. 7 is an explanatory diagram of a separated tooth model, as shown in a sectional view taken along the line 2—2 of FIG. 6.

FIGS. 8 to 10 inclusive show another embodiment of the invention.

FIG. 8 is a plan of another tray surrounded with a frame member.

FIG. 9 is an enlarged perspective view of a pin.

FIG. 10 is a sectional view taken along the line 3—3 of FIG. 8.

FIGS. 11 and 12 show another embodiment of the invention.

FIG. 11 is a perspective view of a tray.

FIG. 12 is a sectional view taken along the line 4—4 of FIG. 11. In FIG. 12, a frame member surrounding the tray and a pin engaged with a hole are added.

Figure 13:
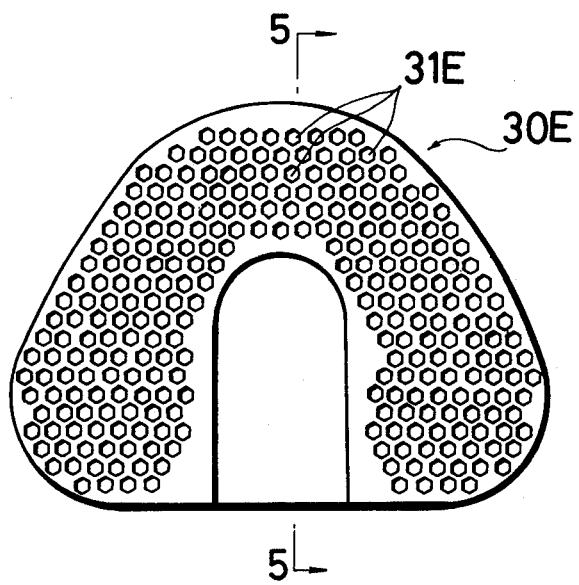
Figure 14:
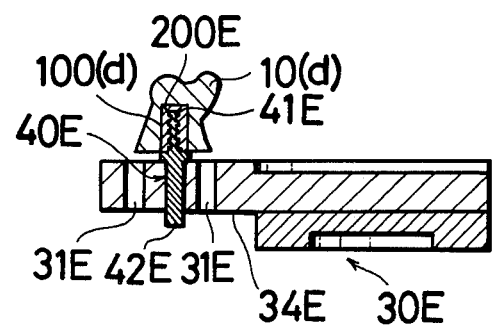

FIGS. 13 and 14 show another embodiment of the invention.

FIG. 13 is a plan of a tray.

FIG. 14 is a sectional view taken along the line 5—5 of FIG. 13. In FIG. 14, a pin and others are added.

The tool of the invention shown in FIGS. 2 to 5 comprises a tray 30 having a plurality of holes 31 made vertically, and pins 40 each capable of being engaged with the holes 31 so that head portions 41 of the pins 40 may be positioned above the tray. The tray 30 has a sunken portion 32 in the surface, and the sunken portion is formed so as to be gradually deepened from the circumference to the central portion of the surface. Also, the surface of the tray 30 is formed in a rough plane having a plurality of projections 33, and the holes 31 each are formed conically. Further, the head portions 41 of the pins 40 each have a rough surface which has been knurled or grooved longitudinally and transversely, and leg portions 42 to be inserted into the holes 31 each are formed in a tapered shape corresponding to the shape of the hole 31. In addition, the back surface of the tray 30 is provided with a hollow 34 so that tips of the pins 40 may be projected into the hollow in order to make removal of the pins from the holes easy.

Accordingly, after the pins 40 are engaged with holes 31 at positions on the tray 30 which correspond to both the back surface 11 of tooth models 10(a), 10(b), which are desired to be separated, and the back surface 11 of teeth row models 10(c), 10(d) to be the rest of a plaster teeth row model 10, the back surface of which has been flatly finished, plaster 20 is newly poured into the sunken portion 32 so that head portions 41 of the pins 40 each may be embedded in the plaster, and then the plaster teeth row model 10 is put on the plaster 20 and adheres to the plaster at the back surface 11. Of course, it is possible to make grooves in the back surface 11 of the teeth model. After the plaster 20 has been hardened, the teeth row model 10 is cut at both sides 101, 102, 103 of the tooth model 10(a), 10(b) up to the bottom of the plaster 20, and the separated tooth models 10(a), 10(b) are obtained. The tray 30 does not adhere, because the tray has been commonly made from ABS resin and so on.

On making use of the tool of the invention the, following advantages are obtained: It is unnecessary to make holes to be engaged with pins in the plaster teeth row model, and then pour plaster to fasten the pins in the holes. It is unnecessary to wait until the plaster has been hardened. Accordingly, the work performed with the tool of the invention is much simplified and made easy thus the, and total time necessary for the work is shortened. Since the amount of the plaster 20 combined with the teeth row model 10 is a small quantity enough to embed the head portions of pins 40, the amount of poured plaster is reduced to one-tenth of the amount commonly used. The frame member is unnecessary. Each pin 40 is able to be vertically engaged without skill. Separated tooth models 10(a), 10(b) are easily taken out. Since the surface of the tray 30 is formed to be rough, it is not feared that separated tooth models rattle owing to clearances which are made when the teeth row model is cut into the separated tooth models.

Figure 5:
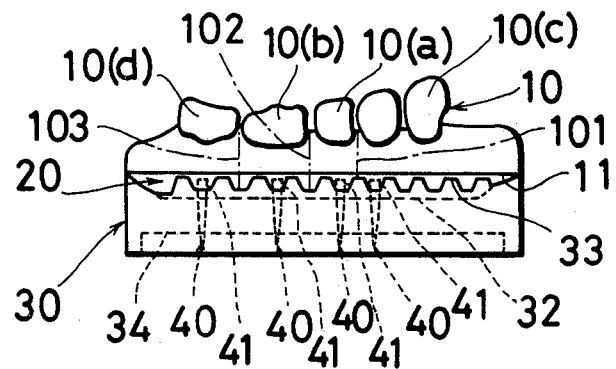
FIG. 5 is an explanatory diagram showing a method for making separated tooth models by means of this embodiment.
Figure 6:
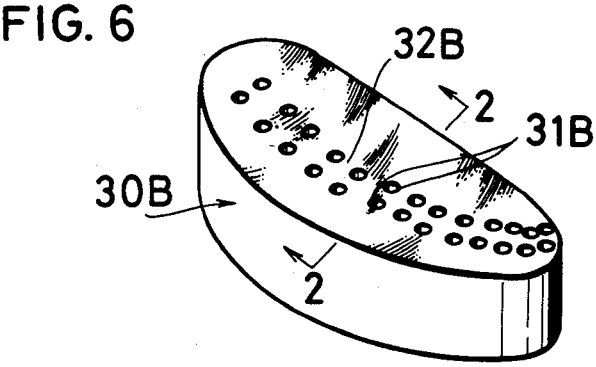
FIGS. 6 and 7 show another embodiment of the invention.
Figure 7:
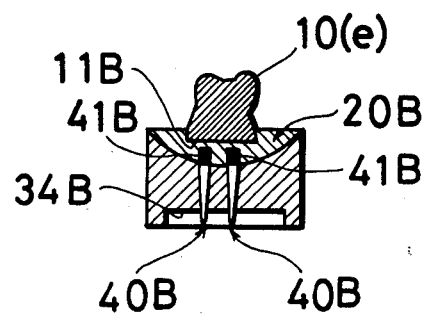

The tool according to another embodiment of the invention shown in FIGS. 6 and 7 comprises a tray 30B having a plurality of holes 31B and a sunken portion 32B in the surface of the tray, said holes each being made in a conical shape and said sunken portion being so formed that the sunken portion is deepened gradually from the circumference to the center portion of the surface, and pins 40B each capable of being engaged with the holes so that head portions 41B of each of the pins are positioned above the surface of the tray. The pins 40B are identical with those used in the embodiment shown in FIGS. 2 to 5. On the back surface of the tray 30B a hollow 34B is Provided so that the tips of the pins 40B are projected into the hollow for the purpose of making removal of the pins easy.

Accordingly, after each pair of pins 40B have been engaged with a pair of holes 31B on the tray 30B at positions which respectively correspond to the back surface 11B of a tooth model 10(e) desired to be separated and the back surface of remaining portion of a teeth row model (not shown), the back surface of which has been flatly finished, plaster 20B is newly poured into the sunken portion 32B so that the head portions 41B of the pins 40B are embedded in the plaster. Then the teeth row model is put on and adheres to the plaster 20B at the back surface 11B. After the plaster 20B has been hardened, the teeth row model is cut at both sides of the tooth model 10(e) desired to be separated up to the bottom of the plaster 20B, and then the separated tooth model 10(e) is obtained. In this embodiment the same effect as described in the embodiment shown in FIGS. 2 to 5 is obtained.

Further, the tool according to another embodiment of the invention is shown in FIGS. 8 to 10. The tool comprises a tray 30C having a flat surface and a plurality of holes 31C made vertically in the surface, pins 40C each capable of being engaged with said holes 31C so that head portions 41 of the pins each are positioned above the surface of the tray, and a frame member 50 releasably fastened to the side wall 35C of the tray 30C so as to form an embankment 51 arround the surface of the tray 30C. The shape of the holes 31C is hexagonal and the back surface of the tray 30C is provided with a hollow 34C which enables the tips of the pins 40C to project into the hollow, for the purpose of making removal of the pins 40C engaged with the holes 31C easy. Head portions 41C of the pins 40C are so shaped that the pins may be prevented from revolving and removing out of the holes after the plaster embedding the head portions has been hardened. The shape of the leg portions 42C of the pins is hexagonal, and capable of being inserted into and engaged with the holes 31C, and accordingly the pins are prevented from revolving. The frame member 50 is made from elastic material such as rubber and plastic.

Accordingly, after pins 40 are engaged with holes 31C of the tray 30C at positions which correspond to the back surface of a tooth model (not shown) desired to be separated and the back surface of the rest of a teeth row model (not shown), the back surface of which has been flatly finished, a frame member 50 is fastened around the tray 30C to make an embankment 51. Then, plaster (not shown) is newly poured into the embankment 51 formed around the surface of the tray 30C. After head portions 41C of the pins 40C are embedded in the plaster, a teeth row model is put on the plaster, and then the back surface of the teeth row model adheres to the plaster. After the plaster has been hardened, the frame member 50 is removed from the tray 30C, and the teeth row model is cut at both sides of a tooth model desired to be separated up to the bottom of the plaster. Thus a separated tooth model is obtained. The tool according to this embodiment can exhibit the same effects as those of the embodiment shown in FIGS. 2 to 5.

The tool according to another embodiment of the invention is shown in FIGS. 11 and 12. The tool comprises a tray 30D having a flat surface and a plurality of holes 31D made vertically in the surface, the flat surface being provided with grooves formed longitudinally and transversely in the surface, pins 40D each capable of being engaged with the holes so that head portions 41D of the pins are positioned above the surface of the tray, and a frame member 50B releasably fastened around the side wall of the tray 30D so as to form an embankment 51B around the surface of the tray. The shape of the holes 31D and the shape of the pins 40D to be engaged with the holes is the same as those of the holes 31 and the pins 40 shown in FIGS. 3 and 4. Further, both a hollow 34D in the back surface of the tray and the frame member 50B are the same as both the hollow 34C and the frame member 50 shown in FIGS. 8 and 10, and accordingly a detailed explanation is omitted. This embodiment requires the frame member, but can exhibit the same effect as that of the foregoing embodiment shown in FIGS. 2 to 5.

The tool according to another embodiment of the invention is shown in FIGS. 13 and 14. The tool comprises a tray 30E having a flat surface and a plurality of holes 31E made vertically in the surface, and pins 40E each capable of being engaged with the holes 31E so that head portions 41E of the pins are positioned above the surface. The holes 31E are the same as the holes 31C shown in FIGS. 8 and 10, and also the pins 40E are the same as the pins 40C shown in FIG. 9.

Accordingly, the back surface of a plaster teeth row model is flatly finished. Then, a hole 100(d) is made at a position in the back surface of a tooth model 10(d) desired to be separated, and a hole (not shown) is made at a position in the back surface of the rest of a teeth row model (not shown). Pins 40E are engaged with holes 31E of the tray 30E, the holes correspond respectively to the foregoing two holes. Plaster 200E is poured into the holes made in the back surface of the teeth row model, and head portions 41E of the pins 40E adhere to the teeth row model. A separated tooth model is obtained by cutting the teeth row model at both sides of the tooth model desired to be separated up to the bottom of the back surface.

According to the embodiment, steps have to be performed for making holes in a plaster teeth row model and pouring plaster into the holes to make head portions of the pins, which have been engaged with holes of the tray, adhere to the teeth row model, but plaster newly combined with the back surface of the teeth row model is quite unnecessary. Accordingly, the quantity of used plaster is reduced so much. Since it is easy to cut the plaster teeth row model, the total time for the steps is shortened. In addition, the embodiment has the following advantages which are the same as those of the embodiment shown in FIGS. 2 to 5: No frame member is required. It never requires skill to arrange the pins vertically on the tray. Removal of a separated tooth model is easy. It is not feared that the separated tooth model rattles because of the clearances made when the tooth model has been separated.

I claim:

1. A tool for making separated tooth models comprising:
    a tray having a plurality of holes made vertically in the surface of said tray, the tray having a sunken portion in the surface thereof gradually deepening from the circumference of said tray to the central portion of the surface of said tray, and
    a plurality of pins, each of said pins having a leg portion and a head portion, wherein said leg portion is removably engaged with said holes and said head portion is positioned above the surface of said tray.

2. A tool according to claim 1, wherein the holes are arranged in at least two rows.

3. A tool according to claim 1, wherein the holes are conical and said leg portion of each pin is tapered.

4. A tool according to claim 1 wherein in use the head portion of each pin is embedded in plaster and wherein said head portion of each pin is shaped such that the pins cannot rotate or come out of the holes after the head portion is embedded in plaster.

5. A tool according to claim 1, wherein the holes and the pins are shaped such that the pins cannot rotate.

6. A tool for making separated tooth models according to claim 1 wherein the tray includes a side wall surrounding said surface and further including
    a frame member releasably fastened around the side wall of said tray so as to form an embankment around the surface of said tray.

7. A tool for making separated tooth models according to claim 1 further including
    a frame member releasably fastened around the periphery of the tray so as to form an embankment around the surface of the tray, the embankment enclosing the head portions of the pins to define a space for the introduction of a material to embed the head portions.

* * * * *